United States Patent [19]
Nalepa et al.

[11] Patent Number: 5,969,219
[45] Date of Patent: Oct. 19, 1999

[54] "AWN-INHIBITOR GENES OF TRITICALE AND THEIR USE"

[75] Inventors: Stanislaw Nalepa, Salinas; George Fohner, Gilroy, both of Calif.

[73] Assignee: Resource Seeds, Inc., Gilroy, Calif.

[21] Appl. No.: 08/759,867

[22] Filed: Dec. 3, 1996

[51] Int. Cl.[6] ............................. A01H 5/10; A01H 5/00; A01H 1/04
[52] U.S. Cl. ........................ 800/320; 800/260; 435/410
[58] Field of Search ..................... 800/200, 205, 800/250, DIG. 55, DIG. 58; 47/58, DIG. 1

[56] References Cited

PUBLICATIONS

Abstract for J.Leslie South Dakota Farm & Home Research 37(2)21–22 (1986).
Article for J. Leslie South Dakota Farm & Home Research 37(2)21–22 (1986).
Cholick, K. M. Et al, Registration of Marval Triticale (Crop Sci. 28:1031–1032, 1988).
Reddy et al. Induction of useful mutants in hexaploid triticale (xTriticosecale Wittmack), by irradiating plants at different developmental stages. Genetica Agraria, 40:423–431, 1986.
Reddy et al. Cell and tissue culture studies in rice, maize, and triticlae. Indian Review of Life Sciences, 11:29–52, 1991.
Stojkovski et al. Inheritance of awnedness of the ear in hybridization of Triticum aestivum and triticale. Godisen Zbornik na Zemjodelski Fakutet. 39:67–74. Translated, 1994.
Sharma et al. Location of genes for awnedness on specific chromosomes of a wheat (Triticum aestivum)–rye (Secale cereale) recombinant trough monosomic analysis. Indian Journal of Agricultural Sciences. 65:290–292, 1995.

*Primary Examiner*—Douglas W. Robinson
*Assistant Examiner*—Melissa Kimball
*Attorney, Agent, or Firm*—Rothwell, Figg, Ernst & Kurz

[57] ABSTRACT

This invention relates to a triticale plant, seed, cultivar, and hybrid. More specifically, the invention relates to a triticale plant having mutant awn-inhibitor genes that result in an absence or reduction in length of awns. The invention also relates to crossing cultivars, inbreds, and hybrids containing the awn-inhibitor genes to produce novel types, cultivars, and hybrids of completely awnless and short-awn triticale for agronomic purposes.

36 Claims, 2 Drawing Sheets

"AWN-INHIBITOR GENES OF TRITICALE AND THEIR USE"

BACKGROUND OF THE INVENTION

The present invention relates to novel awn-inhibitor genes of triticale that result in the reduction of awn length and produce an awnless characteristic in a number of different genetic backgrounds and environments. The present invention also relates to a triticale seed, a triticale plant, a triticale cultivar, and a triticale hybrid that contain the awn-inhibitor genes. In addition, the present invention is directed to transferring the awn-inhibitor genes in the triticale plant to other triticale plants, and is useful for producing novel types, cultivars, and hybrids of awnless and short-awn triticale.

Triticale (Triticosecale Wittmack) is a genus of plants created by pollinating wheat with rye, then manipulating the resulting genetic combination so that the combined genomes of the wheat and cereal rye are both retained in subsequent generations. With its genetic endowment from wheat and rye, triticale is a new crop plant that ideally combines the yield and quality advantages of wheat, with the hardiness, pest tolerance, and adaptability of rye.

Researchers began crossing wheat and rye in the late 1800's, but fertile triticales capable of producing viable seed were virtually unknown until after 1938. In that year the Swedish geneticist Arne Muntzing produced fertile triticale by treating wheat-rye crosses with colchicine, which doubled the chromosomes so that normal reproductive pairing and division could occur. With normal pairing and division of chromosomes at meiosis, a triticale could be reproduced through subsequent generations. Triticale became a new crop plant, similar to but distinct from wheat and rye and the other cereal grains in its breeding, seed production, and use. Once created and reproduced, a triticale does not "revert" or "break down" to its wheat and rye components. Triticale is primarily a self-pollinated crop like wheat, although as a result of its rye component it does out-cross more frequently than wheat.

Commercial cultivars of triticale first became available in the 1960's in Europe. Acreage in the U.S. began to grow in the 1980's. Currently worldwide acreage of triticale is approximately 6 million, while that in the U.S. is approximately 450,000. Triticale is managed like wheat, though it requires less inputs such as fertilizer, water, and pesticides.

Most of the triticale now grown in the United States is for grazing and harvested forage (hay and silage) for beef and dairy cattle. Triticale competes with other cereal grains, primarily wheat and oats, for these forage markets. These markets in the U.S. are substantial. Annually in the U.S. over 18 million acres of cereal grains are planted for forage production. In the southern Central Plains alone, over 12 million acres of wheat are used for pasture for grazing on average each year. Cereal silage and hay are important in the major dairy producing regions, and cereal hay is a popular forage for horses.

Compared to wheat and oats, triticale has important advantages for forage production in terms of yield, production costs, and tolerance to pests, drought, low fertility, mineral toxicities, and heavy grazing (National Research Council, Triticale: *A Promising Addition to the World's Cereal Grains*, National Academy Press, Washington, D.C., 1989.) Despite the important advantages of triticale over other cereal grains for forage, triticale is now planted on less than 3% of the U.S. cereal forage acreage. A major limitation on the use of triticale for forage has been the presence of awns on triticale. Awns are long needle-like appendages on the flower "pike" or "head" located at the top of the plant. As the flower head emerges from the stem and develops through the stages of flowering and grain development, the awns stiffen and become increasingly irritating and injurious to livestock that graze the plants as pasture, or eat the harvested plants as hay. "Rough awns in small grain hay can cause cattle considerable soreness and irritation to the eyes, mouth, lips, gums, and lower surface of the tongue" as described in Watson, S. L., et al., *Small Grain Cereals for Forage*, Cooperative Extension Service, Kansas State University Publication MF-1072, 1993. Awns can cause injury and infection in livestock, which increase veterinary costs and decrease animal health. Even when injuries do not occur, the presence of awns can reduce feed intake and the profitability of livestock production.

With respect to awns, oats and some wheat cultivars have had an important advantage over triticale. Oats do not have the long, heavy awns that cause problems in pastures or hay. Although some wheat cultivars have awns, others do not. The most popular wheat cultivars for forage production have no awns or very short awns (Carver, B. F., et al., Registration of Three Pairs of Awned vs. Awnleted Near-Isolines of Hard Red Winter Wheat, Crop Science, 33:885, 1993.; Krenzer, G., et al., Wheat Variety Trial Results-1993, Cooperative Extension Service, Oklahoma State University, Department of Agronomy, Publication PT 93-1, 1993; and Weyrich, R. A., et al., Effects of Awn Suppression on Grain Yield and Agronomic Traits in Hard Red Winter Wheat, Crop Science 34:965–969, 1994.)

Although they differ importantly in intraspecies diversity of awn development, wheat and triticale have the same pattern of plant development and morphology, including the development and morphology of heads and awns. The flower heads, or spikes, develop at the top of the main stem and secondary stems called tillers, which are analogous to branches. An individual plant usually has a main stem and multiple tillers, the number of which depends on plant density, soil moisture, nutrient supply, pest damage, seeding date, and temperature, as well as the genetics of the plant. Typically two to four tillers per plant will develop to the point of developing a head, although under conditions of high plant population, stress, or late planting date a plant might have only a main stem. Tillers develop sequentially during growth of the plant. Primary tillers develop one at a time from buds in the crown of the main stem. Secondary tillers may develop from buds in the axils of leaves on primary tillers, and tertiary tillers may develop on secondary tillers. The morphology of an individual tiller, including its awn development, is affected by competition among tillers for light, water, and nutrients, and the environmental conditions under which each tiller initiates and develops. The main stem and each of the tillers develop along a different course of time, and may be exposed to different growing conditions at the stages of growth affecting awn development. The later appearing tillers, however, have fewer leaves so many reach maturity at roughly the same time as the earlier tillers.

Each head at the top of a stem consists of multiple spikelets, each of which consists of multiple florets that produce pollen, ovules, and eventually kernels. Awns are located on bract-like parts of the florets called lemmas. Among wheat cultivars, awn development varies from those essentially lacking awns to those with awns on every lemma exceeding 100 mm. In contrast to wheat, essentially all rye cultivars have awns. Triticale cultivars have awn lengths and frequency exceeding that of the shortest-awned wheat cultivars, perhaps reflecting the influence of its rye genetic component.

Developing a triticale plant having no awns or very short awns, like those of wheat cultivars favored for forage, would provide all of the important benefits of triticale in terms of higher yield, wider adaptability, greater durability, and reduced production inputs, while avoiding the substantial problems associated with awns. With such a triticale, acreage of the crop should increase dramatically, benefiting forage and livestock producers and others involved in the development, production, and use of forages.

Because of these substantial potential benefits, significant plant breeding effort has been directed toward breeding triticale with short or absent awns comparable to those of the wheat cultivars now favored for forage. The most common approach to developing shorter awned triticale has been to use genes responsible for short or absent awns in wheat. The genetics of awn development in wheat is believed to involve the interplay of numerous awn promoter genes (at least thirteen) and three inhibitor genes. In common wheat (*Triticum aestivum*), the three inhibitor alleles have a dominant effect: when present they largely override the awn-promoter genes at the other loci resulting in significantly shorter and fewer awns.

The awn-inhibitor genes in wheat are called "Hooded", "Tipped 1", and "Tipped 2" (International Wheat Genetics Symposium, Proceedings of the Sixth International Wheat Genetics Symposium, Kyoto, Japan, 1983; Molchan, I. M., et al., Genetics of Awnedness and Varietal Reproduction in Winter Wheat, I. Awnedness as a Quantitative Character, Soviet Genetics 16(2):222–229, 1980; Molchan, I. M., et al., Genetics of Awnedness and Varietal Reproduction in Winter Wheat, II—The Nature of the Dominance of the Degree of Expression of Awns in the Spike, Soviet Genetics 16(3) :320–326, 1980; Molchan, I. M., et al., Genetics of Awn Development and Varietal Reproduction in Winter Wheat, III—Nature of Segregation After Crossing of the Forms Differing in Degree of Awn Expression in the Spike, Soviet Genetics 17(10):1211–1216, 1982; and Watkins, A. E., et al., Variation and Genetics of the Awn in Triticum, J. of Genetics XL (1 &2):243–273, 1940.) "Hooded" is of limited commercial significance, and results in short, broad awns that are curved inward into a hood shape. Tipped 1 and 2 account for the absent and reduced awn characteristic that is of commercial importance in wheat. Tipped 1 results in very short or absent awns at the base of the head, while awns increase in length toward the top of the head. Tipped 2 results in uniformly short awns over the entire head. Plants that are homozygous for both Tipped 1 and 2 inhibitor alleles have heads that either have no awns or very short awns depending on promoter genes and modification factors. Plants with the various other combinations of homozygous and heterozygous Tipped 1 and 2 have reduced awns of various lengths, frequencies, and positions on the head (Molchan, I. M., et al., Genetics of Awnedness and Varietal Reproduction in Winter Wheat, I. Awnedness as a Quantitative Character, Soviet Genetics 16(2):222–229, 1980; Molchan, I. M., et al., Genetics of Awnedness and Varietal Reproduction in Winter Wheat, II—The Nature of the Dominance of the Degree of Expression of Awns in the Spike, Soviet Genetics 16(3) :320–326, 1980; and Watkins, A. E., et al., Variation and Genetics of the Awn in Triticum, J. of Genetics XL (1 & 2):243–273, 1940.) The Tipped 1 and 2 genes are hereafter referred to in this discussion as the wheat awn-inhibitor genes.

Although the "wheat awn-inhibitor" (WAI) genes are considered dominant, the extent of that dominance, and hence the length and frequency of awns, depends on which inhibitor alleles are present and on the interaction of the inhibitors, promoters, and other endogenous and exogenous modifiers as shown in Table 1. As a result of modified expression of the awn genes in wheat, awn lengths often differ among plants of the same cultivar, heads on the same plant, and even among spikelets on the same head.

TABLE 1

Factors Determining Awn Length in Wheat

Multiple genes promoting awn development (at least 13 loci)
    Combination of alleles at these loci establish potential awn development.
Wheat awn inhibitor alleles
    In wheat, three alleles are dominant inhibitors of awn development, and to a large extent override the awn promoters. These three awn inhibitors have a much weaker effect on awn length and frequency in triticale than they do in wheat.
Endogenous Factors Regulating Gene Expression for Awns
    Cytoplasmic modifiers that enhance the effect of awn-inhibitor genes.
    Factors associated with location of spikelet on head, i.e. basal, mid, apex.
    Factors associated with location of head on plant, i.e. early, mid, or late tiller.
Exogenous Factors Regulating Gene Expression for Awns
    Drought
    High temperatures The complexity and variability of the genetic and environmental basis of awn frequency and length can make description and classification of awnedness difficult and subjective. The term "awnless", for example, has been used imprecisely and diversely in both scientific literature and commercial trade. Some authors have classified as "awnless" any heads that are not fully awned, i.e. that lack the same frequency and length of awns as related fully awned forms (Miller, E. C., et al., A Study of the Morphological Nature and Physiological Functions of the Awns of Winter Wheat, Kansas State College of Agriculture & Applied Science, Technical Bulletin 57, 1944; Molchan, I. M., et al., Genetics of Awnedness and Varietal Reproduction in Winter Wheat, I. Awnedness as a Quantitative Character, Soviet Genetics 16(2):222–229, 1980.) Others have classified as "awnless" only those heads that have no discernable awns, i.e. no lemma extensions exceeding 1 to 2 mm (Bayles, B. B., et al., Classification of Wheat Varieties Grown in the United States in 1949, United States Department of Agriculture Technical Bulletin No. 1083, 1954.) Most authors have adopted a classification for "awnless" heads that is intermediate to these extremes, in many cases using vague, qualitative criteria for their classification (Molchan, I. M., et al., Genetics of Awnedness and Varietal Reproduction in Winter Wheat I. Awnedness as a Quantitative Character, Soviet Genetics 16(2):222–229, 1980; Molchan, I. M., et al., Genetics of Awnedness and Varietal Reproduction in Winter Wheat, II—The Nature of the Dominance of the Degree of Expression of Awns in the Spike, Soviet Genetics 16(3) :320–326, 1980; Watkins, A. E., et al., Variation and Genetics of the Awn in Triticum, J. of Genetics XL (1 & 2):243–273, 1940.) In addition to "awnless" and "awned", some classifications include "awnleted" for heads with awns that are reduced but still clearly present, and "apically awnleted" for heads that only have awns on the top spikelets. In commercial trade, the term "beardless" is often used to describe cultivars having short or no awns, while "bearded" is used for those with long awns (Bayles, B. B., et al., Classification of Wheat Varieties Grown in the United States in 1949, United States Department of Agriculture Technical Bulletin No.1083, 1954.)

The confusion and misreporting associated with classification and reference to awn length is exemplified by a research publication from South Dakota State University in 1986 announcing the development of the triticale variety "Marval", with the claim: "Marval is thought to be the only awnless variety of triticale" (J. Leslie, South Dakota Farm & Home Research, vol. 37 (2): p21–22, 1986.) However, the official Registration description issued by the breeders of "Marval" described the variety as "awnletted", indicating that "Awns are 5 to 10 mm long at the base of the spike and 10 to 35 mm long at midspike. Marval's awnletted spike is the primary distinguishing feature when compared to other triticale cultivars." (Cholick, F. A., et al., Registration of 'Marval' Triticale, Crop Science, v 28:1031, 1988.)

The publications associated with the release of "Marval" exemplify how the term "awnless" has been used erroneously in published descriptions of grain varieties and plants, and highlight the inherent variability within varieties, plants, and heads in the expression and description of awn lengths, which in the case of "Marval" vary between 5 and 35 mm depending on place on the head and other variables. The emphasis of these publications on awn length also underscores the major significance of awn length for triticale, and the extent and duration of efforts to reduce it in triticale. At the time "Marval" was released, having heads (spikes) with awns no longer than 35 mm was a notable improvement over other triticale varieties, although those heads would not even be classified as semi-awned under currently proposed standards as shown in Table 2.

Classifying plants in terms of awnedness can be even more difficult than classifying individual heads because an individual plant usually has multiple heads, which may differ in terms of their awn length and frequency. The difficulties of classification are compounded further for some cultivars because microenvironmental effects may cause plants of a population of that cultivar to differ in the frequency and length of awns even though they are genetically the same.

Previous attempts to reduce awn length in triticale have involved producing or crossing triticale with wheat cultivars having the WAI ("Wheat Awn Inhibitor") genes. The focus on the WAI genes was logical because triticale originated from wheat and rye, and awn inhibition is common in wheat but virtually nonexistent in rye. In wheat, the WAI genes can result in cultivars for which awns are absent or very short and infrequent. Unfortunately the use of WAI genes or any other factors associated with awn inhibition in wheat have repeatedly and consistently failed to achieve the degree of awn inhibition in triticale that is achievable in wheat. The inadequacy of the WAI genes for triticale may be related to the strong expression of awn development in rye.

In addition to failing to produce a completely awnless triticale, use of the WAI genes has proved to be slow and unpredictable for producing even short-awned cultivars of triticale. To date, the short-awned cultivars of triticale have erratic awn lengths and lower marketability and value than would be true for a product with inhibited awn development comparable to the preferred forage wheats. The failure of the substantial past efforts using WAI genes suggests that the use of those genes alone will not produce awnless triticale. The reliance on the WAI genes appears to have been an obstacle to achieving a triticale with inhibited awn development comparable to the preferred forage wheats.

The reliance on the WAI genes also appears to have been an obstacle to the development and production of $F_1$ triticale hybrids having short awns. In triticale, as in many other crops, use of $F_1$ hybrids could provide tremendous benefits by combining complementary advantages from genetically different parent plants and achieving the added synergistic effect ("hybrid vigor") often associated with combining different genetic types. Triticale is well suited for production of $F_1$ hybrid seed. In contrast to wheat, for example, triticale has more prolific pollen production and dispersal, more open flowering, and a longer pollination period, all of which facilitate production of hybrid triticale seed. Substantial yield heterosis in triticale provides ample economic benefits to justify the added cost of hybrid seed. By combining the high yields and other advantages of $F_1$ hybrids with the advantages of short awns, an awnless or short-awn $F_1$ triticale would have important economic value.

SUMMARY OF THE INVENTION

The present invention relates to a triticale seed, a triticale plant, a triticale awn, a triticale cultivar, and a triticale hybrid and a method for producing a triticale plant.

More specifically, the invention further relates to awn-inhibiting genes that produce a triticale plant with reduced awn length and produce an awnless characteristic in a number of different genetic backgrounds and environments. One object of the present invention is to reduce the awn length, increase the palatability of triticale forage (pasture, silage, and hay) to livestock, and decrease the risk of injury to livestock caused by awns.

The present invention further relates to triticale plants with one or more heads having all awns shorter than 4 mm. The invention also relates to triticale plants having one or more inverted awns.

The invention further relates to a triticalae variety or triticale $F_1$ hybrid wherein at least 80 percent, or alternatively 60 percent, 40 percent or 20 percent of the heads have a long-awn length of less than 10 mm. The invention further relates to triticale varieties and hybrids wherein less than 20 percent, or alternatively 10 percent, 5 percent or 2 percent of the heads have a long-awn length of greater than 20 mm.

The present invention further relates to a method of producing the disclosed triticale plants and seeds by crossing an awnless or short-awn triticale plant of the instant invention with another triticale plant. The invention also relates to the transfer of the genetic awnlessness and reduced awn length into other triticale plants.

DETAILED DESCRIPTION OF THE INVENTION

Figure 1:
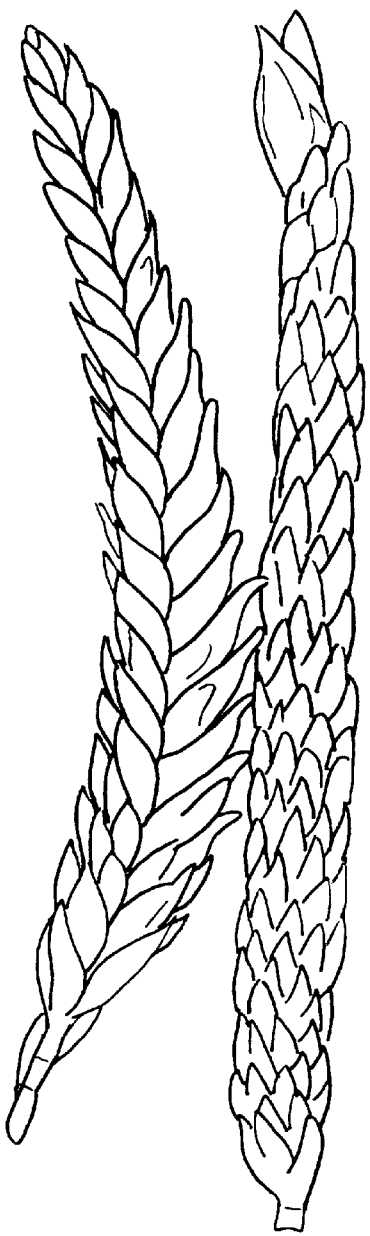
FIGS. 1–4 show schematic views of triticale heads having various awn lengths including the awnless characteristic.
Figure 2:
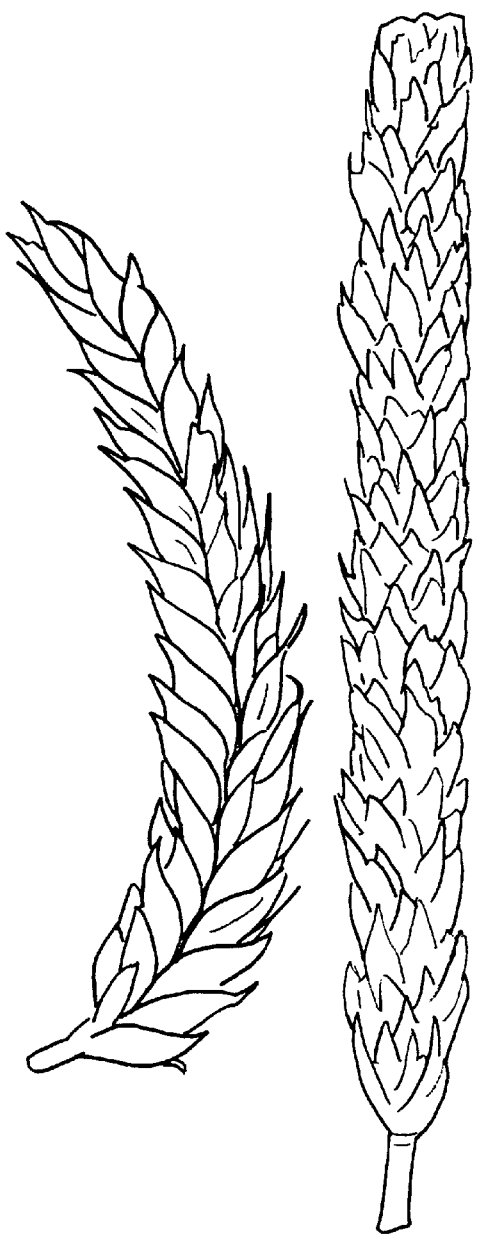
Figure 3:
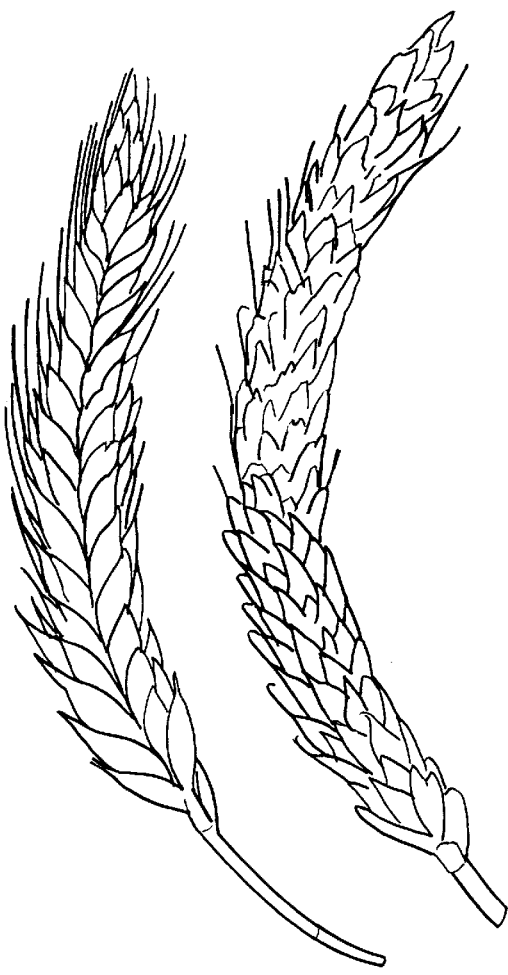
Figure 4:
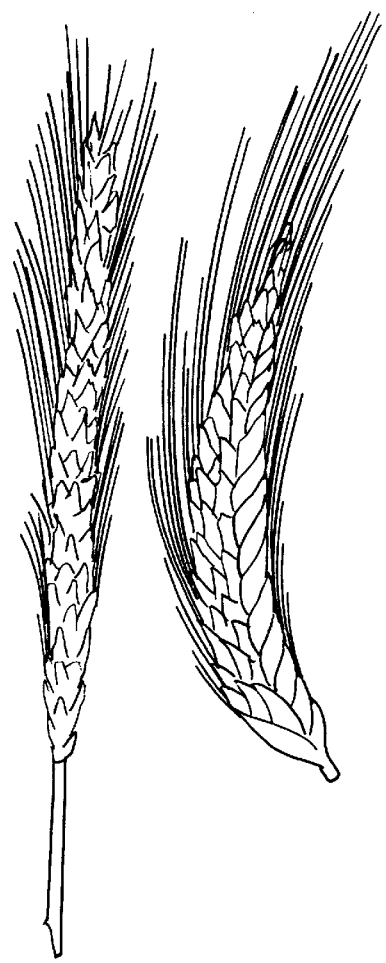

In order to provide an understanding of several of the terms used in the specification and claims, the following definitions are provided:

Apically Awned Triticale Head: The term "apically awned triticale head" is intended to mean a triticale head that has one or more awns longer than 20 mm on one or more of the top 30% of the spikelets on the head, but no awns longer than 20 mm on the lower 70% of the spikelets on the head.

Apically Awnleted Triticale Head: The term "apically awnleted triticale head" is intended to refer to a triticale head that is completely awnless except for awns ranging in length between 2 mm and 20 mm on the top 30% or less of the spikelets.

Awn: The term "awn" is intended to mean the elongated needle-like appendages on the flower- and seed-bearing "head" at the top of a cereal grain plant (e.g. triticale, wheat, rye). These awns are attached to the lemmas. Lemmas enclose the stamen and stigma as part of the florets. These florets are grouped in spikelets, which in turn together comprise the head.

Awned Triticale Head: The term "awned triticale head" is intended to refer to a triticale head that has awns exceeding 20 mm in length on at least 90% of the spikelets.

Awnleted Triticale Head: The term "awnleted triticale head" is intended to refer to a triticale head having awn lengths between 2 mm and 20 mm.

Bearded: The term "bearded" is intended to describe cereal grain plants that have long awns.

Beardless: The term "beardless" is intended to describe cereal grain plants that are awnless, awnleted, apically awnleted, or merely have shorter awns than other varieties.

Awnless Triticale Head: The term "awnless triticale head" is intended to refer to a triticale head having no awns which exceed 2 mm in length.

Head: The term "head" means a group of spikelets at the top of one plant stem. The term "spike" also refers to the head of a plant located at the top of one plant stem.

Inverted Awns: The term "inverted awns" is intended to refer to awns that bend sharply toward the base of the head rather than the awn extending toward the apex of the head. The first and only known occurrence of inverted awns on triticale resulted from crossing plants containing the triticale awn-inhibitor genes of the present invention into a few genetic backgrounds. In addition to being inverted, the inverted awns are unusually thin.

Long-awn: The term "long-awn" is intended to refer to the longest awn on a head, also called a spike, of a grain plant.

Long-awn Length: The term "long-awn length" is intended to refer to the length of the longest awn on a head.

Mutation Breeding: The term "mutation breeding" is intended to refer to the use of mutagenic agents (e.g. chemical, radiation) to increase the frequency of mutant plants useful in the breeding of improved cultivars.

Semi-Awned Triticale Head: The term "semi-awned triticale head" is intended to refer to a triticale head that has awns exceeding 20 mm in length which are located on more than the top 30% of the spikelets but on less than 90% of the spikelets.

Triticale Awn-inhibitor (TAI) Genes: The term "triticale awn-inhibitor (TAI) genes" is intended to refer to novel awn-inhibitor alleles of the present invention, believed to be two alleles and which are capable of reducing the length and frequency of awns in triticale to levels comparable to those in the shortest-awned wheat cultivars, including completely awnless triticale.

Wheat Awn-inhibitor (WAI) Genes: The term "wheat awn-inhibitor genes" is intended to refer to three alleles identified as "Tipped 1", "Tipped 2", and "Hooded" found at three independently segregating loci in wheat. The alleles are dominant in wheat, largely overriding the awn-promoter genes at other loci resulting in significantly shorter and fewer awns. Wheat plants that are homozygous for both Tipped 1 and 2 in some cases are completely awnless, depending on the awn-promoter genes and other modification factors. Wheat plants with the various other combinations of homozygous and heterozygous Tipped 1 and 2 have reduced awns of various lengths, frequencies, and positions on the head. The WAI genes also inhibit awn development in triticale, but to a much lesser extent than in wheat.

As used herein, the term "plant" includes plant cells, plant protoplasts, plant cells of tissue culture from which triticale plants can be regenerated, plant calli, plant clumps, and plant cells that are intact in plants or parts of plants such as pollen, flowers, seeds, leaves, stems, and the like. Tissue culture of triticale is described in Zimny, J., et al., Fertile, Transgenic Triticale (x Triticosecale Wittmack), Molecular Breeding 1:155–164, 1995.

TABLE 2

Awn Classification for the Triticale Head
Based on Length, Frequency, & Position of Awns on the Head (Spike)

| | |
|---|---|
| Longest Awn is Less than or equal to 2 mm on the head | Awnless |
| Longest awn is longer than 2 mm and less than or equal to 20 mm, | |
| Awns exceeding 2 mm on no more than the top 30% of the spikelets. | Apically Awnleted |
| Awns exceeding 2 mm on spikelets positioned over the full length of head. | Awnleted |
| Longest awn longer than 20 mm, | |
| Awns exceeding 20 mm on no more than the top 30% of spikelets. | Apically Awned |
| Awns exceeding 20 mm on more than the top 30% but less than 90% of the spikelets. | Semi-awned |
| Awns exceeding 20 mm on at least 90% of spikelets. | Awned |

The triticales of the present invention reproducibly express the awn-reduction characteristic. This novel awn length reduction characteristic has been expressed in many different genetic backgrounds of triticale. The genetic factor of the present invention capable of transmitting the absence or shortening of awns is believed to be two mutant genes developed by Resource Seeds, Inc. via mutation breeding. It is a feature of the present invention that these two genes may be used in and transferred into the various triticale cultivars and hybrids.

The present invention is directed to developing unique awnless, apically awnleted, and awnleted plants of triticale. Prior to the present invention, a completely awnless triticale (i.e., plant having no awns longer than 2 mm) had not been developed. Furthermore, except for the present invention, no triticale cultivar or hybrid had attained awns as uniformly short as the short-awned and awnless wheat cultivars. The shortest-awned triticale cultivars available prior to the present invention have substantially more awns in frequency and length than do the shortest-awned wheat cultivars.

Prior to the present invention, the triticale lines containing short-awned plants were inadequate for producing short-awned $F_1$ hybrids for commercial use. No short-awned $F_1$ triticale hybrids for commercial use were produced using the WAI genes or any other previous approach. Even at the research level, no $F_1$ populations of triticale with awn lengths comparable to those of the shortest-awned wheat were produced. Crosses with previously developed shortest-awned triticale plants produced $F_1$ triticale plants having awn lengths and frequencies that are unpredictable and intermediate to that of the two parents. Consequently, prior to the present invention, it was not possible to produce an $F_1$ hybrid having awn reduction comparable to those of the present invention.

The triticale of the present invention expresses an absence of awns in many genetic backgrounds, and a substantial reduction in length of awns in all other backgrounds. The novel transferable awn-inhibitor genes of the present invention are two genes. These genes allow the development of the first known completely awnless triticale plant, and the shortest known awnleted triticale plant. In addition to including plants that have shorter awns than ever before seen in triticale, the awn-inhibitor genes of the present invention result in populations of plants that collectively have substantially less awn development, both in frequency and length, than any population of previously developed triticale. The overall development of awns across an entire plant population reflects the effects of endogenous and environmental modifiers as well as the genetics of awn promoters and inhibitors. Although the shortest-awned populations of triticale developed prior to the present invention occasionally include the categories of awnleted and apically awnleted heads, the frequency of these heads is significantly lower and the frequency of awned and semi-awned plants significantly higher than is true of plant populations of triticale cultivars and hybrids of the present invention.

Prior to the present invention, it was not possible to achieve the same degree of awn suppression in triticale as is possible in wheat. In addition to lacking any completely awnless heads like those found in wheat and in triticale of the present invention, the shortest-awned triticale cultivars produced previously had substantially more awns (in frequency and length) to deter feeding and cause injury than did the shortest-awned wheat cultivars. The present invention makes it possible for the first time to achieve the objective of producing triticale cultivars and hybrids that have inhibited awn development like that of the shortest-awned wheat cultivars.

The genes of the present invention overcome the significant obstacles and limitations associated with past attempts to develop awnless and short-awn triticale and the methods used to breed them. The present invention results in triticale cultivars and hybrids that have fewer awns and shorter awns (including completely awnless triticale), greater value for forage, and greater market appeal. The present invention provides improved means of breeding and producing triticale cultivars and $F_1$ hybrids.

In their extensive analysis of the inheritance of awns, Molchan, I. M., et al., Genetics of Awnedness and Varietal Reproduction in Winter Wheat, I. Awnedness as a Quantitative Character, Soviet Genetics 16(2):222–229, 1980 found very high correlation between the number of awned spikelets on a head and the length of the longest awn on that head, and concluded that length of the longest awn was an excellent index of overall awnedness. Accordingly, they used measurements of longest awn per head ("long-awn") to classify wheat populations as to their awn development. The same approach is adopted here for triticale, and provides an efficient method of classifying populations of triticale plants according to commercially meaningful differences in awn development.

EXAMPLES

The following examples are provided to further illustrate the present invention and are not intended to limit the invention beyond the limitations set forth in the appended claims.

Example 1

Development of Awn-inhibitor Genes

The awn-inhibitor characteristic of the present invention resulted from chemical mutation beginning in 1982. In 1982 seeds of the triticale cultivar, Lasko, were treated with a chemical mutagen with the goal of producing novel alleles. The mutated seed was then planted to produce seed, which was harvested in the spring of 1983. The process of planting and harvest was repeated in the 1983–84 growing season. The seed from the 1983–84 season was planted in the fall of 1984, and in spring of 1985 seed was harvested from plants exhibiting desirable characteristics, primarily reduced plant height and plumper kernels. In addition, some of the plants harvested in the spring of 1985 had notably shorter awns than the fully-awned Lasko cultivar, although none were awnless, apically awnleted or awnleted.

Some of the seed from plants selected for harvest in 1985, including short-awned plants from plot 2930-85, were treated again with a chemical mutagen in the fall of 1985. This was the second mutation treatment. This mutated seed was then planted and the resulting plants allowed to self-pollinate to produce seed, which was harvested in the spring and planted in the fall of 1986. The resulting plants were selected in the spring of 1987 on the basis of desirable characteristics, primarily reduced plant height, kernel plumpness, and reduced awn length. The process of seed harvest, planting, and re-selection was repeated in 1987–88 with harvest in the spring of 1988.

In the 1990–91 growing season, a cross was made between two short-awned breeding lines derived through the above described series of mutagen treatments, plantings, plant selections, and harvests. Seed from this cross was harvested and planted in a greenhouse to produce $F_2$ seed that was planted in the field in 1991–92. Unexpectedly, one of the $F_2$ lines (A-M-124) had completely awnless plants. These awnless plants were the first known completely awnless triticale, and this was the first time that a triticale had attained the degree of awn-inhibition found in wheat.

Subsequent self-pollination of the awnless plants and crosses with a diverse group of awned triticale has shown the awnless characteristic to be reproducible and transferable. The genetics and developmental mechanism by which this stronger inhibition of awns was achieved by the TAI (Triticale Awn Inhibitor) genes of present invention have not yet been completely elucidated. Because the inadequacy of the WAI genes for triticale may be related to the strong expression of awn development genes in rye, it is probable that the TAI genes in some way inhibit that strong effect of the rye genome.

Example 2

Inheritance of Awnless and Reduced-Awn Characteristics

Preliminary studies of the plants of the present invention suggested a mode of inheritance of the awnless and reduced-awn characteristic that is more complex than that which would result from a single gene locus. Subsequent analysis suggested the involvement of two gene loci that together strongly affected awn presence and length, with some additional variation resulting from secondary modifier genes and the environment.

A general model consistent with the observed results is presented in Table 3. In that table, the alleles responsible for absent or shortened awns, each associated with a different locus, are represented as "$TAI_1$" and "$TAI_2$". According to this generalized model of the TAI genes, genotypes having at least one of the awn-inhibiting alleles at each loci result in completely awnless, apically awnleted, or occasionally awnleted phenotypes depending on the modifying effects of the specific genetic background, stem location, and the environment. Genotypes homozygous for awn-inhibition at either of the loci, while homozygous for non-inhibition at the other, result in semi-awned or occasionally awnleted phenotypes again depending on the modifying effects of the specific genetic background, stem location, and the environment. Those genotypes with only one awn-inhibiting allele result in semi-awned phenotypes, or occasionally awned phenotypes (like those of the double homozygous non-inhibitor) when awn development is favored by strong awn promoters and/or environmental conditions. This model presumes the absence of any additional secondary awn-inhibitors such as the WAI genes. Their presence may result in fewer awned and semi-awned and more awnleted phenotypes.

Awn frequency and lengths in the second ($F_2$) generation from crosses involving plants having the novel awn inhibitors of the present invention strongly suggest that two independently segregating mutant co-inhibitors are involved. The two treatments with chemical mutagens have produced two mutations resulting in dominant changes that disrupt awn development.

TABLE 3

| Alleles at Locus 1 | Alleles at Locus 2 | Phenotype |
| --- | --- | --- |
| $TAI_1\ TAI_1$ | $TAI_2\ TAI_2$ | Awnless/Awnleted |
| $TAI_1\ tai_1$ | $TAI_2\ TAI_2$ | Awnless/Awnleted |
| $TAI_1\ TAI_1$ | $TAI_2\ tai_2$ | Awnless/Awnleted |
| $TAI_1\ tai_1$ | $TAI_2\ tai_2$ | Awnless/Awnleted |
| $TAI_1\ TAI_1$ | $tai_2\ tai_2$ | Semi-Awned/Awnleted |
| $tai_1\ tai_1$ | $TAI_2\ TAI_2$ | Semi-Awned/Awnleted |
| $tai_1\ tai_1$ | $TAI_2\ tai_2$ | Semi-Awned/Awned |
| $TAI_1\ tai_1$ | $tai_2\ tai_2$ | Semi-Awned/Awned |
| $tai_1\ tai_1$ | $tai_2\ tai_2$ | Awned |

Example 3

Differences Between Present Invention and Prior Cultivars

Triticale cultivars and hybrids of the present invention differ significantly from all previously developed triticale genetically, morphologically, and in economic value as shown in Table 4. With respect to genetic differences, when crossed with fully awned triticale, triticale having the TAI genes have produced $F_1$ plants having short or no awns like the TAI parent, reflecting the dominance of the TAI genes. In contrast, when crossed with fully awned triticale, all previously developed reduced-awn triticales produce $F_1$ plants having significantly longer and more frequent awns than the reduced-awn parent, reflecting no dominance.

TABLE 4

Novel Characteristics of TAI Genes of the Present Invention

Stron dominance in inhibiting development of awns.
Completely awnless heads in certain genetic backgrounds.
Inverted awns in certain genetic backgrounds.
Cultivars and $F_1$ hybrids consisting of plant populations that include heads with no awns longer than 4 mm.

With respect to morphological differences, triticale of the present invention include completely awnless heads (no awns longer than 2 mm), heads with no awns longer than 4 mm, and heads with inverted awns, all of which are features never before found in triticale.

With respect to differences in economic value as they would be used commercially, triticale of the present invention have far fewer and shorter awns, including some completely lacking awns, than any triticale cultivars available to date, resulting in higher feed palatability and lower risk of injury to livestock. Although the shortest-awned populations of triticale developed prior to the present invention occasionally include apically awnleted heads, the frequency of those heads is significantly lower and the frequency of awned and semi-awned plants significantly higher than is true of plant populations of triticale cultivars and hybrids of the present invention. Also, in terms of economic value for plant breeding, the genetic dominance of the awn inhibition of the present invention provides a means of developing short-awned triticale cultivars and hybrids more quickly, reliably, and with less cost than was possible previously.

The achievement of awnlessness in triticale through mutation breeding, compared to the failure of previous attempts to achieve it with WAI genes or any other previously tried approach, indicates that these mutations have overcome the apparently dominant effect of the rye genome in triticale that in the past prevented the expression of awnlessness.

Example 4

Comparison with Current Commercial Triticales

Prior to the present invention, the triticale variety with the shortest awns was TRICAL® Brand 102, owned by Resource Seeds, Inc. and commercially released in 1994. "102" is technically classified as being awnleted (U.S. Plant Variety Protection Certificate No. 9400201), but is commonly described in the trade as "beardless" or "almost awnless" and is sometimes referred to as the "awnless" triticale when being distinguished from other triticale varieties.

Variety "102" has significantly shorter awns than the commercial triticale variety "Jenkins", which is an awned triticale variety. In adjacent plots grown under identical conditions in Hollister, Calif., the average length of the longest awn per head on triticale "102" was 17.3 mm and the median was 15.5 mm, compared to an average of 65.8 mm and median of 68.5 mm for "Jenkins". Twenty-five percent (25%) of the "102" heads had a long awn of 12 mm or less, compared to 55 mm or less for the shortest 25% of the "Jenkins" heads. The head with the shortest awns had a long-awn length of 5 mm for "102" compared to 25 mm for "Jenkins".

In characterizing awn lengths of "102" triticale, the effect of growing conditions must be taken into account. Awn lengths on crops grown from the same seed lot of "102" triticale in four locations exemplify the effects of environment on awn development. The average long-awn length varied among growing conditions from 17.3 mm in Hollister, California to 19.9 mm in Woodland, Calif., a significant difference statistically ($p<0.05$). Median long-awn varied from 15.5 mm in Hollisterto 19.5 mm in Woodland. Minimum long-awn varied from 5 mm in Hollister to 9 mm in Woodland. Twenty-five percent (25%) of the "102" heads had a long awn of 12 mm or less in Hollister, compared to 16 mm in Woodland. Of the 669 heads of "102" inspected over the four locations, including both random samples and directed search for the shortest awns, the head with the shortest long-awn had a long-awn of 5 mm.

Triticale "102" has substantially shorter awns than "Jenkins" and other triticale varieties, but is clearly not truly "awnless". Awn lengths achievable with the TAI awn-inhibitor genes of the present invention are significantly shorter than those found in variety "102". That significant difference is demonstrated by comparisons at two locations between "102" and three $F_4$ populations derived from crosses involving the TAI genes: lines 3303, 3304, and 3305 as shown in Table 5. Comparisons were made at each of the two locations on the basis of long-awn lengths of the 20 heads having the shortest awns in 7 $m^2$ plots. Since the data suggested that the variance of long-awn length of "102" was larger than that of the TAI populations, comparisons were made by t-test assuming unequal variances.

Awn lengths achievable with the TAI genes of the present invention were significantly shorter than those found in "102" at both locations (p<0.001) for all three populations derived from crosses with the TAI genes as shown in Table 6. For the three TAI populations, long-awn length averaged over the shortest 20 heads, together averaged 1.9 mm in Texas and 2.7 mm in California compared to 9.5 mm and 15.1 mm for "102". Environmental conditions as reflected in differences between locations had a significant effect (p<0.001 by ANOVA F test both with and without including "102" in the analysis). The effect of environment was much more pronounced in absolute terms for "102" than for the TAI populations. For each of the three TAI populations the difference between the Texas and California was 1 mm or less in terms of mean, minimum, and 25% percentile, while medians differed by 1.5 mm or less. Completely awnless heads (no awns exceeding 2 mm) were achieved with the TAI genes of the present invention while none were found in the "102".

Even at the research level it has not been possible to produce $F_1$ populations of triticale with awn lengths comparable to those of the shortest-awned wheat. Consequently, prior to the present invention, it would not have been possible to produce an $F_1$ hybrid having awn development comparable to those of the shortest-awned wheat, or to those of the present invention.

Examples 5 to 14

Examples 5–14 involve crosses made between triticale A-M-124 or its cytoplasmicly male sterile analog, both of which carry the TAI genes, and an awned triticale. In all the examples, all heads of the $F_1$ plants were completely awnless, apically awnleted, or awnleted, demonstrating the strong dominance of the TAI genes. In the $F_2$ populations, large variation was observed with respect to length of awns, as would be expected from genetic segregation of the TAI genes along with secondary effects from modifier genes and environmental variation. Heads of $F_1$ and $F_2$ plants were classified according to criteria described in Table 2. A primary criterion for classification is the length of the longest awn on the head, which has been shown to correlate well with overall awn development of the genotype (total frequency and length of awns) (Molchan, I. M., et al., Genetics of Awnedness and Varietal Reproduction in Winter Wheat, I. Awnedness as a Quantitative Character, Soviet Genetics 16(2):222–229, 1980; Molchan, I. M., et al., Genetics of Awnedness and Varietal Reproduction in Winter Wheat, II—The Nature of the Dominance of the Degree of Expression of Awns in the Spike, Soviet Genetics 16(3):320–326, 1980.)

Example 5

Completely awnless A-M-124 having the TAI genes was crossed with the awned cultivar Malno. All $F_1$ plants obtained from the cross had completely awnless to awnleted heads, reflecting the strong dominance of the awn-inhibitor genes in A-M-124 as shown in column 2 of Table 7. As reported in columns 3 and 4 of the same table, the observed $F_2$ population included 101 completely awnless to awnleted heads, and 70 heads with longer and more frequent awns, which provided a good fit to a 9:7 ratio expected if inheritance of the awn-inhibitor trait is governed by two complementary dominant genes, allowing for minor variation in awn length resulting from secondary modifier genes and environmental effects as shown in column 5–8, of Table 7.

TABLE 5

Length of awns on the 20 heads in population having shortest "long awn"
(20 shortest "long awns" in the population)

| | Farwell, TX | Woodland, CA | Farwell, TX | Woodland, CA | Farwell, TX | Woodland, CA | Farwell, TX | Woodland, CA |
|---|---|---|---|---|---|---|---|---|
| Pedigree | 3303 | 3303 | 3304 | 3304 | 3305 | 3305 | 102 | 102 |
| Range | 1–5 | 2–5 | 0.5–2 | 1–3 | 0.5–2 | 1–3 | 6–12 | 9–19 |
| MIN | 1 | 2 | 0.5 | 1 | 0.5 | 1 | 6 | 9 |
| MAX | 5 | 5 | 2 | 3 | 2 | 3 | 12 | 19 |
| AVG | 2.68 | 3.55 | 1.43 | 2.33 | 1.70 | 2.15 | 9.45 | 15.05 |
| SD | 1.18 | 0.83 | 0.49 | 0.83 | 0.47 | 0.67 | 2.11 | 1.74 |

TABLE 6 t Test - Probabilities
Compared to Triticale Cultivar "102"

| Pedigree | Farwell, TX | Woodland, CA |
|---|---|---|
| 3303 | <.001 | <.001 |
| 3304 | <.001 | <.001 |
| 3305 | <.001 | <.001 |

TABLE 7

| Awned Male Parent | $F_1$ Phenotype | Observed $F_2$ (n = 171) | | Expected $F_2$ (9:7) | | $X^2$ | p |
|---|---|---|---|---|---|---|---|
| | | Awnless & Awnleted | Semi-Awned & Awned | Awnless & Awnleted | Semi-Awned & Awned | | |
| Malno | Awnless & Awnleted | 101 | 70 | 96 | 75 | 0.6 | >.25 |

Example 6

Completely awnless A-M-124 having the TAI genes was crossed with the awned triticale line XA217. The $F_1$ plants all had apical awnlets, again reflecting the strong dominance of the awn-inhibitor genes in A-M-124 as shown in column 2, Table 8. As reported in columns 3 and 4, the observed $F_2$ population included 164 completely awnless to awnleted heads, and 146 heads with longer and more frequent awns, which provided a good fit to a 9:7 ratio expected if inheritance of the awn-inhibitor trait is governed by two complementary dominant genes, again allowing minor variation in awn length resulting from secondary modifier genes and environmental effects as shown in column 5–8, Table 8.

TABLE 8

| Awned Male Parent | $F_1$ Phenotype | Observed $F_2$ (n = 310) | | Expected $F_2$ (9:7) | | $X^2$ | p |
|---|---|---|---|---|---|---|---|
| | | Awnless & Awnleted | Semi-Awned & Awned | Awnless & Awnleted | Semi-Awned & Awned | | |
| XA217 | Apically Awnleted | 164 | 146 | 174 | 136 | 1.31 | >.25 |

Example 7

Completely awnless A-M-124 having the TAI genes was crossed with the awned cultivar Grace. All $F_1$ plants obtained from the cross had completely awnless to awnleted heads, again reflecting the strong dominance of the awn-inhibitor genes in A-M-124 as shown in column 2 of Table 9. As reported in columns 3 and 4 of the same table, the observed $F_2$ population included 156 completely awnless to awnleted heads, and 123 heads with longer, more frequent awns, which provided an almost exact fit to the expected 9:7 ratio as shown in column 5–8, Table 9.

TABLE 9

| Awned Male Parent | $F_1$ Phenotype | Observed $F_2$ (n = 279) | | Expected $F_2$ (9:7) | | $X^2$ | p |
|---|---|---|---|---|---|---|---|
| | | Awnless & Awnleted | Semi-Awned & Awned | Awnless & Awnleted | Semi-Awned & Awned | | |
| Grace | Awnless & Awnleted | 156 | 123 | 157 | 122 | 0.01 | >.90 |

Example 8

Completely awnless A-M-124 having the TAI genes was crossed with the awned triticale line XE335. All $F_1$ plants obtained from the cross had completely awnless to awnleted heads as shown in column 2 of Table 10. As reported in columns 3 and 4 of the same table, the observed $F_2$ population included 74 completely awnless to awnleted heads, and 54 heads with longer, more frequent awns, which provided a good fit to the expected 9:7 ratio as shown in column 5–8, Table 10.

TABLE 10

| Awned Male Parent | $F_1$ Phenotype | Observed $F_2$ (n = 128) | | Expected $F_2$ (9:7) | | $X^2$ | p |
| --- | --- | --- | --- | --- | --- | --- | --- |
| | | Awnless & Awnleted | Semi-Awned & Awned | Awnless & Awnleted | Semi-Awned & Awned | | |
| XE335 | Awnless & Awnleted | 74 | 54 | 72 | 56 | 0.13 | >.50 |

Example 9

Awnless A-M-124 was crossed with the awned triticale variety Presto. The $F_1$ plants were completely awnless or with apical awnlets as shown in column 2 of Table 11. As reported in columns 3 and 4 of the same table, the observed $F_2$ population included 196 completely awnless to awnleted heads, and 160 heads with longer, more frequent awns, which provided a good fit to the expected 9:7 ratio as shown in column 5–8, Table 11.

TABLE 11

| Awned Male Parent | $F_1$ Phenotype | Observed $F_2$ (n = 356) | | Expected $F_2$ (9:7) | | $X^2$ | p |
| --- | --- | --- | --- | --- | --- | --- | --- |
| | | Awnless & Awnleted | Semi-Awned & Awned | Awnless & Awnleted | Semi-Awned & Awned | | |
| Presto | Apically Awnleted | 196 | 160 | 200 | 156 | 0.18 | >.50 |

Example 10

Awnless line A-M-124 was crossed with the awned triticale line XA211. The $F_1$ plants were completely awnless to awnleted as shown in column 2 of Table 12, but the $F_2$ did not segregate in the expected 9:7 ratio as shown in columns 5–8, Table 12. Analysis of segregation data revealed that more completely awnless to awnleted phenotypes and less awned and semi-awned types were observed than expected, suggesting some kind of genetic interaction with a locus or loci in addition to the two TAI genes.

TABLE 12

| Awned Male Parent | $F_1$ Phenotype | Observed $F_2$ (n = 356) | | Expected $F_2$ (9:7) | | $X^2$ | p |
| --- | --- | --- | --- | --- | --- | --- | --- |
| | | Awnless & Awnleted | Semi-Awned & Awned | Awnless & Awnleted | Semi-Awned & Awned | | |
| XA211 | Awnless & Awnleted | 270 | 126 | 223 | 173 | 23.0 | >.005 |

Example 11

Awnless A-M-124 was crossed with the awned triticale line XT027 (later released as the variety TRICAL Brand 2700). The $F_1$ plants had apical awnlets as shown in column 2 of Table 13. The $F_2$ data, 187 completely awnless to awnleted, 130 heads with longer, more frequent awns, provided a good fit to the expected 9:7 ratio as shown in columns 5–8, Table 13.

TABLE 13

| Awned Male Parent | $F_1$ Phenotype | Observed $F_2$ (n = 317) | | Expected $F_2$ (9:7) | | $X^2$ | p |
|---|---|---|---|---|---|---|---|
| | | Awnless & Awnleted | Semi-Awned & Awned | Awnless & Awnleted | Semi-Awned & Awned | | |
| XT027 | Apically Awnleted | 187 | 130 | 178 | 139 | 1.04 | >.25 |

Example 12

The awnless line A-M-124 was crossed with the awned triticale variety Rondo. The $F_1$ plants had apical awnlets as shown in column 2, Table 14. The $F_2$ population did not segregate in the expected 9:7 ratio as shown in columns 5–8, Table 14. Analysis of segregation data revealed that more completely awnless to awnleted phenotypes and less awned and semi-awned types were observed than expected, suggesting some kind of genetic interaction with a locus or loci in addition to the two TAI genes.

TABLE 14

| Awned Male Parent | $F_1$ Phenotype | Observed $F_2$ (n = 118) | | Expected $F_2$ (9:7) | | $X^2$ | p |
|---|---|---|---|---|---|---|---|
| | | Awnless & Awnleted | Semi-Awned & Awned | Awnless & Awnleted | Semi-Awned & Awned | | |
| Rondo | Apically Awnleted | 78 | 40 | 66 | 52 | 4.94 | <.05 |

Example 13

The expression of the TAI genes was analyzed in the production of $F_1$ hybrids using female parents having cytoplasmic male sterility. The fertile, awnless line A-M-124 was used as the male parent in the production of two $F_1$ hybrids. Among the heads of the $F_1$ hybrid plants, some were apically awnleted, others expressed enough awn development on the mid and basal spikelets to be classified as awnieted, but still clearly indicated the efficacy of the TAI genes for producing $F_1$ hybrid triticale having the benefits of absent or short awns even in genetic backgrounds favoring awn development as shown in Table 15.

TABLE 15

| Female Parent (Awned) | Male Parent (Awnless) | $F_1$ |
|---|---|---|
| ms $M_{18}$C335 | A-M-124 | Apically Awnleted/Awnleted |
| ms $M_{18}$/20832 | A-M-124 | Apically Awnleted/Awnleted |

Example 14

The expression of the TAI genes also was analyzed in the production of other $F_1$ hybrids using female parents having both the TAI genes and cytoplasmic male sterility. Three of the $F_1$ hybrids had heads all classified as completely awnless or apically awnleted, while two had heads classified as apically awnleted or awnleted as shown in Table 16.

TABLE 16

| Female Parent (Awnless) | Male Parent (Awned) | $F_1$ |
|---|---|---|
| ms $M_{18}$A-M-124 | XS087/XT027 | Awnless to Awnleted |
| ms $M_{18}$A-M-124 | Presto | Awnless to Awnleted |
| ms $M_{18}$A-M-124 | L762 | Awnless to Awnleted |
| ms A-M-124 | XRO66A | Apically Awnleted/Awnleted |
| ms A-M-124 | XT498 | Apically Awnleted/Awnleted |

Example 15

Production of $F_1$ Hybrid Triticale Having the Reduced-Awn Characteristic

Prior to the present invention, the triticale lines containing short-awned plants were inadequate for producing short-awned $F_1$ hybrids for commercial use. In contrast, the TAI genes of the present invention result in the development and production of $F_1$ triticale hybrids that are awnless or have greatly shortened awns. These $F_1$ triticale hybrids combine the advantages of short awns with the yield and overall agronomic advantages from heterosis of $F_1$ hybrids. As a result of the strong dominance of the TAI genes of the present invention, crosses made with a parent line that is homozygous for the TAI genes result in $F_1$ hybrids that are completely awnless or have greatly shortened awns regardless of the awn length of the other parent line. This dominance in most, if not all, genetic backgrounds of triticale makes the TAI genes of the present invention a powerful tool for producing commercial $F_1$ hybrid triticale because only one parent line with the TAI genes is needed. The need for only one parent line with TAI genes greatly speeds the development of superior awnless and short-awned $F_1$ triticale products. By allowing the use of an awned triticale as the other parent line while still producing an awnless or short-awned $F_1$ hybrid, the strong dominance of the TAI genes greatly broadens the choice of potential parent lines for the $F_1$ hybrids, allowing one of them to be chosen on the basis of other desirable characteristics without regard for awn length.

Prior to the present invention, it has not been possible to produce $F_1$ triticale populations with awn lengths comparable to those of the shortest-awned wheat. Awn frequency and length on $F_1$ plants resulting from crosses with what were previously the shortest-awned plants are unpredictable and usually no better than intermediate to that of the two parents. Even for producing $F_1$ hybrids with just reduced awn length, the choice of potential parents would have been very limited, severely compromising the pace and potential for developing reduced-awn $F_1$ hybrids.

Example 16

Comparison of Population Distributions of Awn Lengths

The entire population distribution of awn lengths of a triticale breeding line containing the TAI genes was compared with the population distribution of awn lengths of triticale variety "102". The population of "102" used in the comparison was grown in Hollister, Calif. in 1995–96, and exhibited the shortest awn lengths ever reported for a non-TAI triticale. The TAI line used in the comparison, an $F_3$ selection from a cross between A-M-124 and Lasko-short, and was grown in the same production area in the same year (Gilroy, Calif., 1995–96). The longest awn was measured on each head in the sample populations of the non-TAI triticale and TAI triticale. Each head was then classified based on the length of its longest awn. For the sample population of triticale "102", the non-TAI triticale, only 15% of the heads had a longest awn that was 10 mm or less (i.e. only 15% of the heads did not have an awns excceeding 10 mm); 57% had a longest awn between 11 and 20 mm, and 28% had at least one awn exceeding 20 mm. For the TAI triticale, 87% of the heads did not have any awns exceeding 10 mm; only 12% had a longest awn between 11 and 20 mm, and only 1% had any exceeding 20 mm. Although the population distributions of awn lengths for triticale 102 and the TAI line overlap, they are clearly distinct. The TAI genes resulted in a population distribution of awn length concentrated in the very short awn-length categories, reflecting the strong suppression of awn development by the TAI genes. Further inbreeding and selection of the TAI line, which is still in a relatively early stage of development, would be expected to produce population distributions concentrated even more heavily in the very short awn categories.

As presented in Table 17, the population of triticale plants having the TAI genes had substantially shorter average awn length, more short-awned heads, and substantially fewer long-awned heads than the "102". Eighty-seven percent (87%) of the heads of the TAI population did not have any awns longer than 10 mm (long-awn not longer than 10 mm), while only 15% of the best non-TAI population ("102") were that short. Ninety-nine percent (99%) of the TAI population did not have any awns longer than 20 mm (long-awn not longer than 20 mm), while only seventy-two percent (72%) of the "102" met that standard. Expressed in terms of long-awned heads, only one percent (1%) of the TAI population had awns longer than 20 mm, while twenty-eight percent (28%) of the "102" did.

TABLE 17

Comparison of Awn Lengths of TAI Population and Shortest-Awned Non-TAI Population (Triticale Variety "102")

| Length of Longest Awn Per Head (i.e., "Long-awn Length") | TAI Triticale Line | Triticale Variety "102" |
|---|---|---|
| Population Average (Mean) | 7 mm | 17 mm |
| Population Standard Deviation | 4 mm | 7 mm |
| Population Minimum | 3 mm | 5 mm |
| % of heads having no awn > 5 mm | 37% | 1% |
| % of heads having no awn > 10 mm | 87% | 15% |
| % of heads having no awn > 20 mm | 99% | 72% |

DEPOSIT INFORMATION

Triticale seeds have been placed on deposit with the American Type Culture Collection (ATCC), Rockville, Md. 20852, under Deposit Accession Number 97741 on Sep. 26, 1996.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A triticale seed comprising a dominant awn-inhibiting allele for reduced awn length, wherein said allele is present in the triticale line deposited under ATCC accession number 97741.

2. A triticale plant produced by growing seed of claim 1.

3. The plant of claim 2, wherein said plant further comprises one or more heads having all awns shorter than 2 mm.

4. The plant of claim 2, wherein said plant further comprises one or more heads having all awns shorter than 3 mm.

5. The plant of claim 2, wherein said plant further comprises one or more heads having all awns shorter than 4 mm.

6. The triticale plant of claim 2, wherein said plant has one or more inverted awns.

7. Pollen of the plant of claim 2.

8. An ovule of the plant of claim 2.

9. A tissue culture comprising regenerable cells of the plant of claim 2.

10. A plant regenerated from said tissue culture of the plant of claim 9.

11. A method of producing $F_1$ hybrid triticale seed comprising crossing a first parent triticale plant with a second parent triticale plant and harvesting the resulting $F_1$ hybrid triticale seed, wherein said first or second parent is a triticale plant of claim 2.

12. The method of claim 11, wherein said triticale plant is the female plant.

13. The method of claim 11, wherein said triticale plant is the male plant.

14. A first generation ($F_1$) hybrid triticale plant produced by growing said hybrid triticale seed of claim 11.

15. The triticale $F_1$ hybrid plant of claim 14, wherein said plant further comprises one or more heads having all awns shorter than 4 mm.

16. A triticale $F_1$ hybrid plant of claim 14, said plant further comprises one or more heads having all awns shorter than 2 mm.

17. A triticale $F_1$ hybrid plant of claim 14, wherein said plant has one or more inverted awns.

18. A triticale variety comprising a dominant awn-inhibiting allele for reduced awn length, wherein said allele is present in the triticale line deposited under ATCC accession number 97741.

19. The triticale variety of claim 18, wherein at least 80 percent of the heads have a long-awn length of less than 10 mm.

20. The triticale variety of claim 18, wherein at least 60 percent of the heads have a long-awn length of less than 10 mm.

21. The triticale variety of claim 18, wherein at least 40 percent of the heads have a long-awn length of less than 10 mm.

22. The triticale variety of claim 18, wherein at least 20 percent of the heads have a long-awn length of less than 10 mm.

23. The triticale variety of claim 18, wherein less than 20 percent of the heads have a long-awn length of greater than 20 mm.

24. The triticale variety of claim 18, wherein less than 10 percent of the heads have a long-awn length of greater than 20 mm.

25. The triticale variety of claim 18, wherein less than 5 percent of the heads have a long-awn length of greater than 20 mm.

26. The triticale variety of claim 18, wherein less than 2 percent of the heads have a long-awn length of greater than 20 mm.

27. The triticale $F_1$ hybrid of claim 14, wherein at least 80% of the heads have a long-awn length of less than 10 mm.

28. The triticale $F_1$ hybrid of claim 14, wherein at least 60% of the heads have a long-awn length of less than 10 mm.

29. The triticale $F_1$ hybrid of claim 14, wherein at least 40% of the heads have a long-awn length of less than 10 mm.

30. The triticale $F_1$ hybrid of claim 14, wherein at least 20% of the heads have a long-awn length of less than 10 mm.

31. The triticale $F_1$ hybrid of claim 14, wherein less than 20 percent of the heads have a long-awn length of greater than 20 mm.

32. The triticale $F_1$ hybrid of claim 14, wherein less than 10 percent of the heads have a long-awn length of greater than 20 mm.

33. The triticale $F_1$ hybrid of claim 14, wherein less than 5 percent of the heads have a long-awn length of greater than 20 mm.

34. The triticale $F_1$ hybrid of claim 14, wherein less than 2 percent of the heads have a long-awn length of greater than 20 mm.

35. A method for producing a triticale plant having a head with all awns shorter than 2 mm comprising the steps of:
   a) planting in pollinating proximity seed of a triticale genotype having such genetic factors of claim 2, and another triticale genotype;
   b) cultivating triticale plants resulting from said seeds until said plants bear flowers;
   c) emasculating or otherwise preventing pollen production of the plants of either triticale genotype;
   d) cross pollinating or allowing cross pollination to occur between said triticale genotypes;
   e) harvesting seed produced on said plants that were emasculated or on which pollen production was otherwise prevented, and
   f) germinating said harvested seed to produce a triticale plant.

36. Viable triticale seeds and plants and succeeding generations thereof grown from seeds deposited under ATCC Accession No. 97741 on Sep. 26, 1996 and triticale seeds and plants to which the awn-inhibiting alleles are transferred from said deposited seeds in succeeding generations thereof.

* * * * *